United States Patent [19]  [11] Patent Number: 4,883,482
Gandrez et al.  [45] Date of Patent: Nov. 28, 1989

[54] NAPKIN-KNICKERS PROVIDED WITH AN IMPROVED ELASTIC ARRANGEMENT

[75] Inventors: Jean-Francois Gandrez, Sainte Honorine; Jean-Claude Daugan, Bougival, both of France

[73] Assignee: Colgate-Palmolive Company, New York, N.Y.

[21] Appl. No.: 797,067

[22] Filed: Nov. 12, 1985

[30] Foreign Application Priority Data

Dec. 11, 1984 [FR] France ................. 84 17219

[51] Int. Cl.⁴ .......................................... A61F 13/16
[52] U.S. Cl. ................................................ 604/385.2
[58] Field of Search ............... 604/358, 385.2, 386, 604/391

[56] References Cited

U.S. PATENT DOCUMENTS 3,860,003 1/1975 Buell ................................. 604/385.1
4,300,562 11/1981 Pieniak ............................ 604/385.2
4,430,086 2/1984 Repke ............................... 604/385.2
4,515,595 5/1985 Kievit et al. ..................... 604/385.2
4,555,244 11/1985 Buell ................................. 604/385.2
4,601,717 7/1986 Blevins ............................. 604/385.2

FOREIGN PATENT DOCUMENTS 0149999 7/1985 European Pat. Off. ............ 604/386

Primary Examiner—C. Fred Rosenbaum
Assistant Examiner—Denise Whelton
Attorney, Agent, or Firm—N. Blumenkopf; R. C. Sullivan; M. M. Grill

[57] ABSTRACT

A disposable napkin-knickers comprises an impermeable support sheet, an absorbent wad and a fluid permeable upper sheet of two distinct elastic systems on each side of said napkin knickers. The first system is disposed between said support sheet and the wad and is wider than the second elastic system. The second elastic system is of a more stretchable material than the first elastic system.

3 Claims, 4 Drawing Sheets

NAPKIN-KNICKERS PROVIDED WITH AN IMPROVED ELASTIC ARRANGEMENT

BACKGROUND OF THE INVENTION

1. Field of the Invention

The present invention relates to disposable napkin-knickers having a generally rectangular shape and of the type comprising a flexible and impermeable support sheet with an absorbent wad disposed on the support sheet and a flexible and permeable upper sheet covering the absorbent wad and with the upper sheet being fixed in at least a part of its periphery to the support sheet.

2. Description of the Prior Art

Different types of napkin-knickers are known from the prior art among which two essential categories must be specifically mentioned.

In a first category, there are napkin-knickers which are said to be anatomically cut out and comprise, in the conventional manner, an absorbent wad or pad inserted between an impermeable support sheet and a permeable upper sheet, these two sheets being interconnected in the region of their periphery.

In order to moderate the inconvenience felt by the users of the napkin and thus improve their comfort, the coverings and the wad of such napkins are cut out in the crotch so as to reduce the width thereof and thus afford an anatomical shape.

Further, in order to ensure the fluid tightness of these napkins when they are worn by a user, they are provided with an elastic system for creating a barrier for leakages of liquid excrement, this elastic system being simple or multiple, i.e. having respectively two or more than two elastic bands.

Two cut-out shapes have been adopted. On one hand, a cut-out in the shape of an hour-glass associated with an elastic fluid tight system placed at more than 19 mm from the edge of the wad and, on the other hand, an H-shaped cut-out associated with an elastic sealing system placed at less than 19 mm from the edge of the wad.

However, while napkin-knickers belonging to this category substantially improve the comfort to the user, it nonetheless remains that their manufacture, which employs particular cut-outs, has been consequently found to be relatively complex and, therefore, requires costly machines which have the further drawback of only being able to manufacture a given cut-out.

U.S. Pat. No. 4,430,086 discloses a contoured diaper or napkin-knicker, which employs two separate elastic members, each of the same width and material, even though one of the elastic members in an embodiment may be initially tensioned to a greater degree than the other elastic member.

In a second category, the drawings resulting from the construction of special shapes of napkins are avoided in that there are provided napkins having a generally rectangular shape on which there is provided an elastic sealing system comprising one or more elastic bands which are parallel to each other and generally disposed longitudinally along the edge of the napkin or in the region of the absorbent wad, on or under the latter.

Further, in order to perfect the shaping of such napkins to the anatomical shape of the user and, in particular, in the region of the crotch of the user, the width of the napkin is reduced in this region by a folding of the lateral edge portions of the napkin, which at the same time provides a retention pocket in the crotch.

However, the last-mentioned arrangements do not satisfactorily solve the problem posed by the discomfort felt by the user.

SUMMARY OF THE INVENTION

In order to overcome the aforementioned drawbacks, an object of the present invention is to provide a napkin-knickers which has a generally rectangular shape and which is, when used, fluid-tight and comfortable and adapts itself to the anatomical shape of the wearer.

The invention, therefore, provides a disposable napkin-knickers which has a generally rectangular shape of the aforementioned type and which comprises in combination: two distinct elastic systems which extend longitudinally along at least a part of the length of the napkin, the first system being disposed along the edge of the wad on each side of the latter so as to impart thereto an anatomical shape, and the second system being disposed along the edge of the napkin on each side of the latter so as to ensure the fluid tightness when worn by the user.

According to the other features of the invention:

At least in the region of the part of the napkin corresponding to the crotch of a user, a region of each lateral edge outside the wad, and intermediate between the edge of the latter and the edge of the napkin, it is fixed to the napkin so as to form a fold and thereby decrease the width of the napkin.

The second elastic system remains outside the first system.

A better understanding of the invention will be had from the following description of one embodiment which is given solely by way of example, with reference to the accompanying drawings, in which:

DETAILED DESCRIPTION OF THE INVENTION

Figure 1:
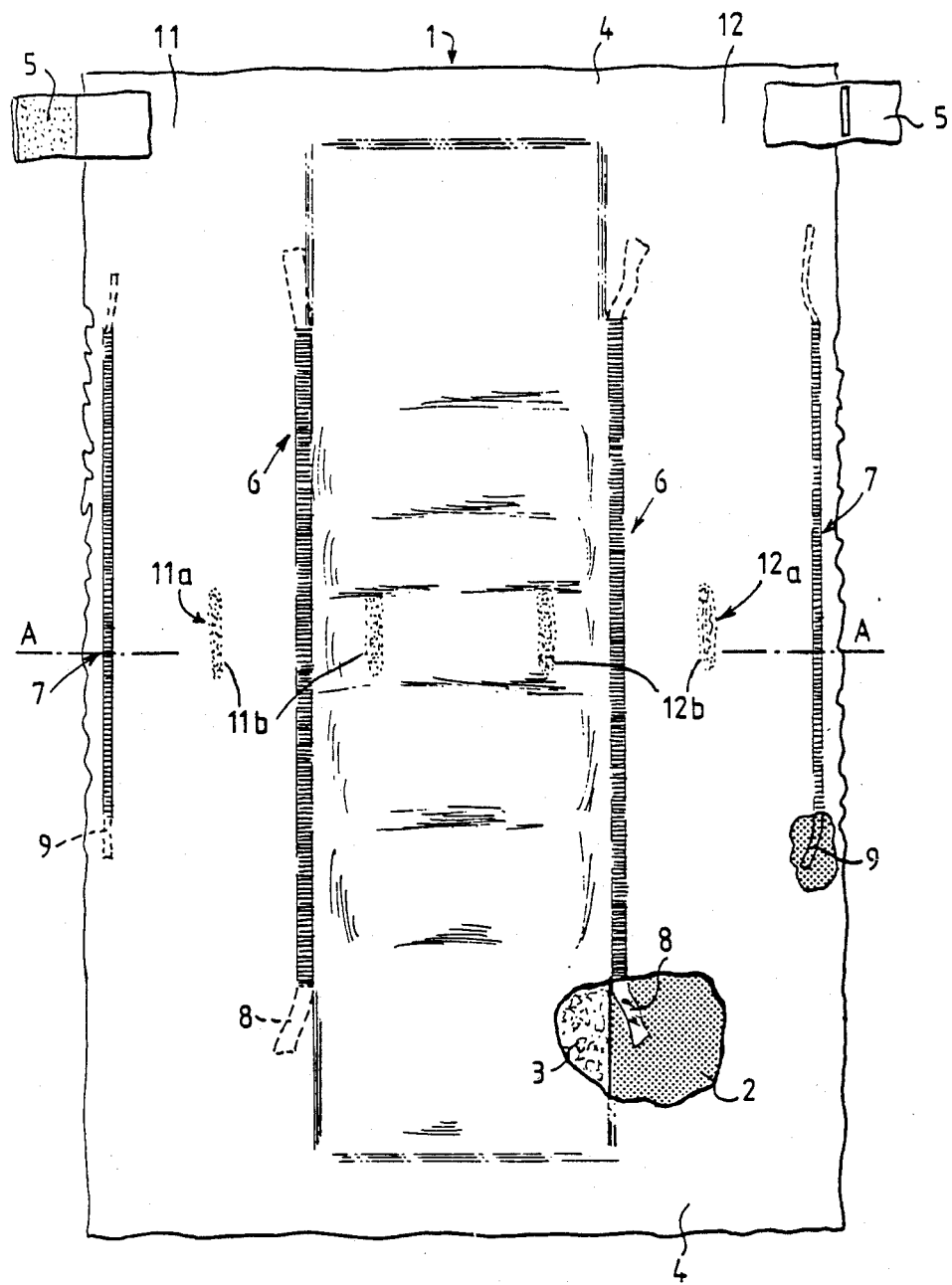
FIG. 1 is a top plan view of a napkin-knickers according to the invention, disposed in the flat and stretched condition.

The disposable napkin-knickers 1, shown in FIGS. 1 through 5, comprises mainly three rectangular elements: a support sheet 2, an absorbent wad or pad 3 and an upper sheet 4.

The absorbent wad 3, for example, of defibrated wood paste, cellulose wool or wadding or any other absorbent material, is disposed on the flexible and impermeable support sheet 2, for example, of polyethylene. The upper flexible and permeable sheet 4, which is permeable in particular to urine and is, for example, of non-woven fabric or a perforated plastic film, covers the absorbent wad 3 and is fixed in the region of its periphery to the periphery of the support sheet 2, for example, by adhesion or thermowelding, so as to form a napkin 1 having a generally rectangular shape (FIG. 1), roughly symmetrical relative to its longitudinal median axis.

Further, in order to ensure the positioning of the napkin 1 on a user, a fixing system is provided at one end of each longitudinal edge of the napkin in the form of an adhesive tape 5 adapted to cooperate with the support sheet 2, on a corresponding side of the opposite end of the napkin 1, when it is placed in position on the user.

According to the invention, the napkin 1 is provided with two distinct, parallel and elastic systems 6, 7 which extend longitudinally along a part of the length of the napkin.

The first elastic system 6 comprises two elastic bands 8, which are disposed along the edge of the absorbent wad 3, on each side of the latter, and fixed under tension between the support sheet 2 and the absorbent wad 3 (FIG. 4), for example, by adhesion or thermowelding.

By way of a modification, the elastic bands 8 may be disposed along the edge of the wad 3 between the support sheet 2 and the upper sheet 4, but the insertion of the elastic bands 8 between the wad 3 and the support sheet 2 is preferred in that their presence between the upper sheet 4 and the wad 3 would result, when the napkin 1 is placed in position on a user, in an excessively close and uncomfortable contact of these elastic bands 8 on the skin of the crotch of the user, while in the chosen arrangement (FIG. 3), the wad 3 substantially reduces this contact.

The second elastic system 7 for ensuring the fluid tightness of the napkin 1 when it is worn by the user, comprises two elastic bands 9, which are disposed on each side and along the edge of the napkin 1, and fixed under tension between the support sheet 2 and the upper sheet 4, for example, by adhesion or thermowelding.

Figure 2:
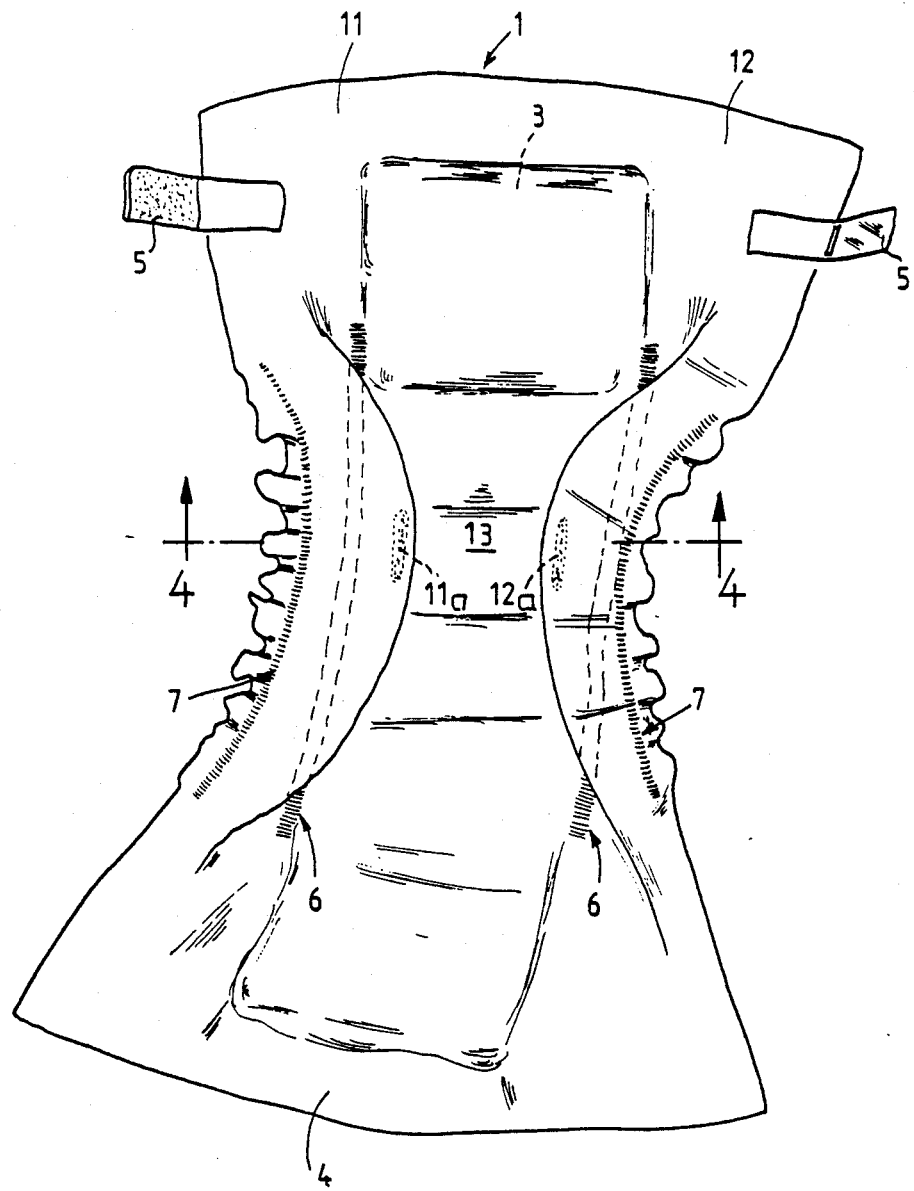
FIG. 2 is a plan view of the top of the napkin-knickers shown in FIG. 1, the latter being in a released condition and a region of its lateral edge portions being folded and adhered to the napkin on top of the wad.
Figure 3:
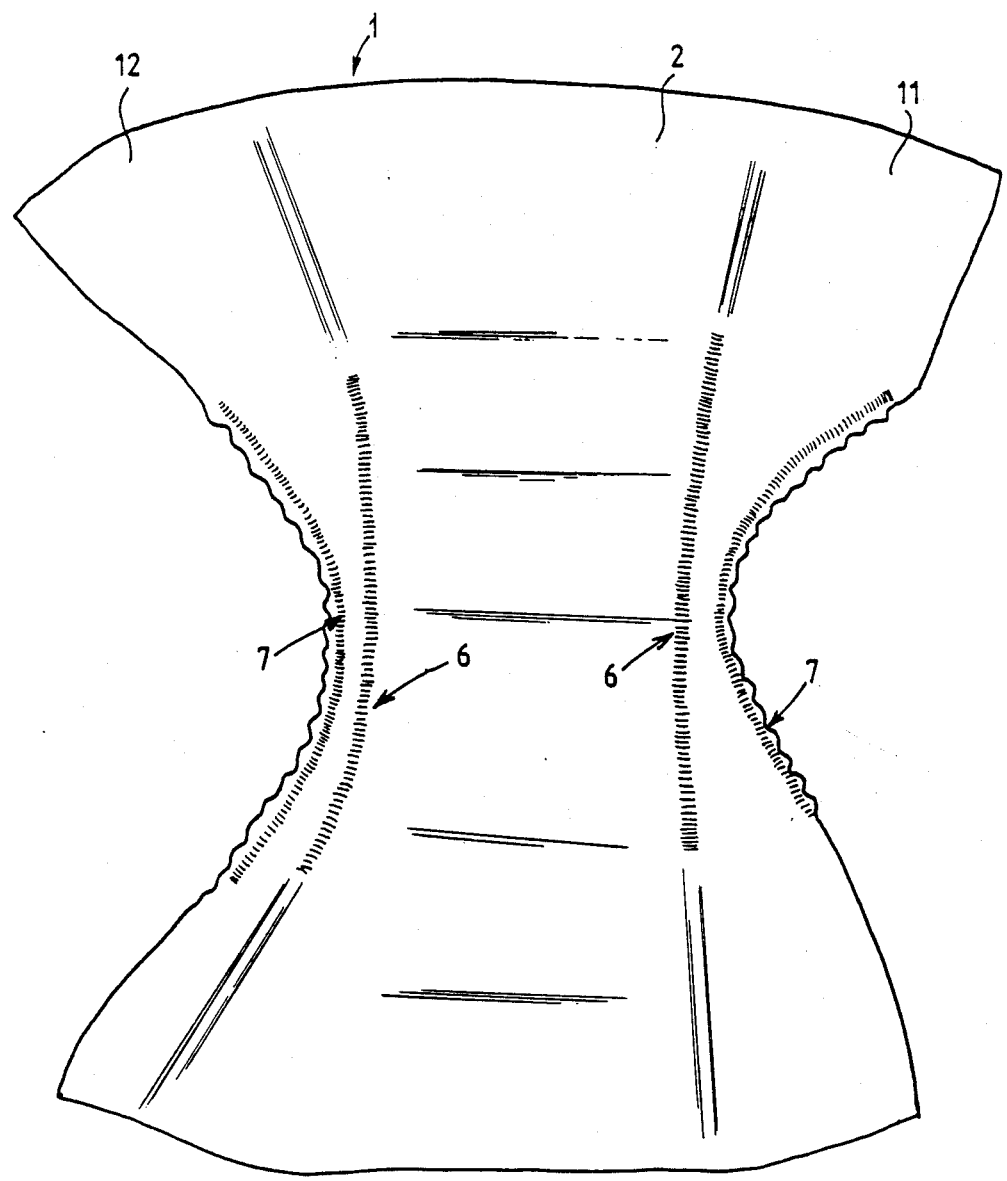
FIG. 3 is a plan view of the top of the napkin shown in FIG. 2.
Figure 4:
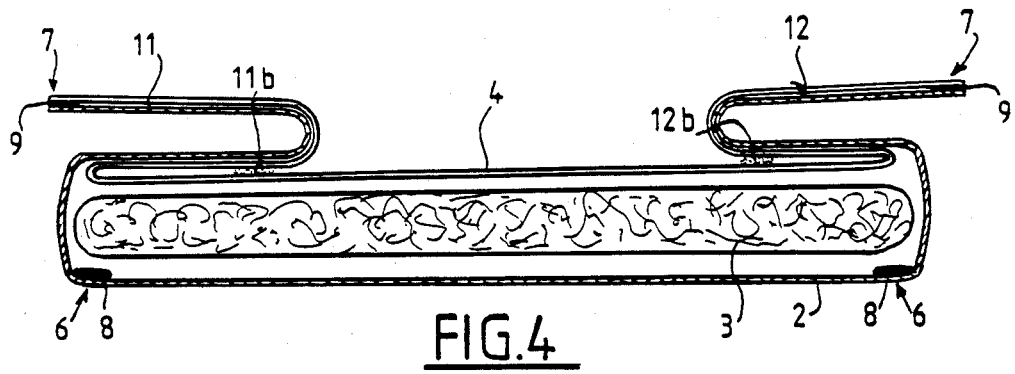
FIG. 4 is a cross-sectional view taken along the plane of line 4—4 in FIG. 2 to an enlarged scale.
Figure 5:
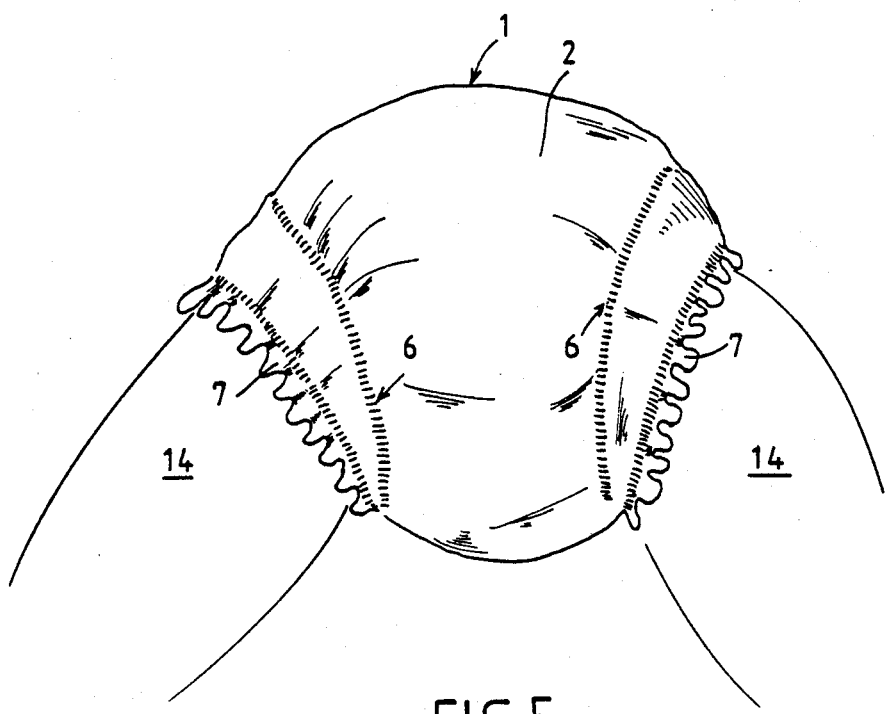
FIG. 5 is a diagrammatic view of a napkin-knickers according to the invention in position on the user.

Further, it will be observed that the arrangement under tension at the edge of the wad 3 of the elastic bands 8 of the first elastic system 6 substantially transversely folds the napkin 1 by bringing the two ends of the upper sheet 4 closer together. This particular shaping of the napkin 1 by this first elastic system advantageously contributes to imparting to the latter a longitudinal anatomical configuration capable of matching the shape of the crotch of the user (FIGS. 2 and 5).

According to a preferred embodiment of the invention, the elastic bands 8 of the first elastic system 6 are wider or have a larger section than the elastic band of the second elastic system 7 which are therefore finer and have a rate of elongation at least equal to that of said elastic bands 8 of the first elastic system 6, this rate of elongation being defined by the following ratio:

$$\text{Rate of elongation} = \frac{l - l\cdot}{l\cdot}$$

wherein l=length of the stretched fixed elastic band, and l=length of the released fixed elastic band.

This choice of the elastic bands 8 and 9 enables those of the first elastic system 6 to ensure preferably a tightening or gripping force on the user which is greater owing to a smaller elongation than that of the second elastic system 7 so as to permit a correct shaping of the absorbent wad 3.

The elastic bands 9 of the second elastic system 7 advantageously ensure a limited tightening or gripping force accompanied by a greater elongation than that of the first elastic system 6 so as to be applied against a large part of the countour of the crotch of the user in the region where the thighs 14 start (FIG. 5).

Further, according to another preferred embodiment of the invention, the elastic bands 8 are fixed symmetrically relative to the transverse median axis A—A (FIG. 1) perpendicular to the longitudinal direction of the napkin 1, and the elastic bands 9 of the second elastic system 7 are offset toward the rear part of the napkin 1, i.e. toward the adhesive tabs 5, so as to well surround the thighs of the user. According to the embodiment shown in the Figures, the offset of said elastic bands 9 is such that about 66% of their length is located on the rear part of the napkin 1, starting at the median transverse axis A—A perpendicular to the longitudinal direction of the napkin. The choice of this value for the rearward offset of the elastic bands 9 is preferred but, by way of a modification, this offset may be such that about 50 to 80% of the length of the elastic bands 9 of the second elastic system 7 is offset toward the rear part of the napkin 1 from the median transverse axis A—A perpendicular to the longitudinal direction of the napkin.

In order to complete the aforementioned longitudinal anatomical conformation afforded by the first elastic system 6, a region 11a, 12a of each lateral edge portion, respectively 11, 12 of the napkin 1, outside the wad 3, and intermediate between the edge of the latter and the edge of the napkin, is advantageously fixed, by means of spots of adhesive 11b, 12b respectively, to the top of this napkin 1.

The regions 11a and 12a located in the part of the napkin 1 adapted to be applied to the region of the crotch of the user, are thus each fixed to a neighboring part of the napkin located above the wad 3 (FIG. 2) and form a lateral fold in the crotch part of the napkin, so that the second elastic system 9 remains outside the first system.

The folding of the lateral edges 11, 12 of the napkin 1 therefore contributes to a reduction in its width in the considered crotch part so as to impart to this napkin an improved transverse anatomical conformation. Further, this folding advantageously forms a kind of retention pocket 13 (FIG. 2) in the part of the napkin which width is thus reduced.

FIG. 5 illustrates the arrangement of the elastic systems 6, 7 when the napkin is worn by the user.

The elastic bands 8 of the first elastic system 6 take up positions in the crotch of the user within the elastic bands 9 of the second elastic system 7 and apply the napkin 1, and in particular the absorbent wad 3, on the user by a longitudinal conformation to the anatomical shape of the user.

The elastic bands 9 of the second elastic system 7 are each applied in the vicinity of the crotch of the user by following the contour of the crotch so as to ensure the fluid tightness of the napkin 1 for possible leakages which might occur where the thighs 14 begin.

This napkin, according to the invention, advantageously combines the comfort of use considering both its adaptation to the morphology of the user and its effectiveness in stopping leakages while being particularly easy to manufacture and consequently at a reasonable cost in that such napkins of generally rectangular shape do not require special and complex cut outs in its various components.

It must be understood that the scope of the invention is not intended to be limited to the embodiments described and illustrated which are merely given by way of example.

Thus, contrary to the direction of folding the lateral portions 11, 12 as before, the latter may, in a modification (not shown), be folded in a similar manner onto the lower side of the napkin by, in this case, fixing the part of the support sheet 2 corresponding to each of the regions 11a, 12a of the lateral portions 11, 12 to a neighboring part of the support 2 located under the absorbent wad 3.

Further, according to another embodiment (not shown), the elastic systems 6, 7 may each comprise more than two elastic bands and, preferably, an even number of elastic bands, so that they may be arranged in two equivalent groups.

What is claimed is:

1. A diposable napkin-knickers having a generally rectangular shape and comprising a flexible and impermeable support sheet, an absorbent wad disposed on the support sheet and a flexible and permeable upper sheet covering the absorbent wad, the upper sheet being fixed in at least a part of its periphery to the support sheet, two distinct systems of elastic bands extending longitudinally in at least a part of the length of said napkin-knickers, the first system comprising two elastic bands disposed between said wad and said support sheet one hand near each edge of said wad so that said wad cushions said first system of elastic bands, said first system imparting an anatomical shape to said napkin-knickers, said second system comprising two elastic bands disposed along the opposite edges of said napkin-knickers so as to ensure fluid tightness thereof when worn by the user, the bands of said first elastic system being substantially wider than the bands of said second elastic system, the material of said bands of said second elastic system being more stretchable than the material of said bands of said first elastic system, the bands of said second elastic system having greater than fifty and less than eighty percent of their length located in the near part of said napkin-knickers measured from a median transverse axis perpendicular to the longitudinal direction of said napkin-knickers.

2. A napkin-knickers according to claim 1, wherein about 66 percent of the length of said elastic bands of said second elastic system is located in said rear part of said napkin-knickers measured from the median transverse axis perpendicular to the longitudinal direction of said napkin-knickers.

3. A napkin-knickers according to claim 1, wherein at least in the region of the part thereof corresponding to the crotch of the user, said second elastic system is disposed on said support sheet outwardly of said wad and adjacent the opposite edges of said napkin-knickers to decrease the width of said napkin-knickers.

* * * * *